United States Patent [19]

Kamogashira et al.

[11] 4,332,891
[45] Jun. 1, 1982

[54] PROCESS FOR THE PRODUCTION OF ANTIBIOTIC CEPHAMYCIN C

[75] Inventors: Takashi Kamogashira; Tsutomu Nishida; Michiharu Sugawara; Tomiyo Nihno; Setsuko Takegata, all of Tokushima, Japan

[73] Assignee: Otsuka Pharmaceutical Co., Ltd., Tokyo, Japan

[21] Appl. No.: 159,568

[22] Filed: Jun. 16, 1980

[30] Foreign Application Priority Data

Jun. 15, 1979 [JP] Japan ................................. 54-75830

[51] Int. Cl.$^3$ ............................................ C12P 35/08
[52] U.S. Cl. ...................................... 435/48; 435/886
[58] Field of Search ........................................... 435/48

[56] References Cited

U.S. PATENT DOCUMENTS 3,865,693  2/1975  Arai et al. ............................. 435/48
4,256,835  3/1981  Kawamura et al. .................. 435/48

*Primary Examiner*—Alvin E. Tanenholtz
*Attorney, Agent, or Firm*—Sughrue, Mion, Zinn, Macpeak and Seas

[57] ABSTRACT

A process for producing an antibiotic Cephamycin C which comprises cultivating a strain of Streptomyces sp. OFR 1022 in a culture medium to accumulate therein Cephamycin C and recovering said Cephamycin C.

3 Claims, 4 Drawing Figures

PROCESS FOR THE PRODUCTION OF ANTIBIOTIC CEPHAMYCIN C

BACKGROUND OF THE INVENTION

1. Field of the Invention

This invention relates to a process for the production of an antibiotic Cephamycin C.

2. Description of the Prior Art

Cephamycin C is a known antibiotic designated as 7-(5-amino-5-carboxyvalerylamino)-3-carbamoyloxymethyl-7-methoxy-3-cephem-4-carboxylic acid and having the following plane formula:

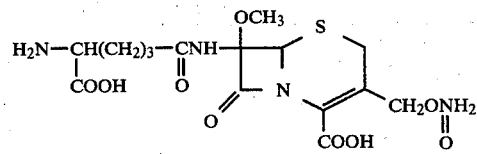

Various processes have heretofore been proposed to produce Cephamycin C using various Streptomyces strains. For example, S. jumonjiensis, S. lactamgenes, S. sp. P6621, S. clavuligerus, S. lactamdulans have been used as described in U.S. Pat. Nos. 3,770,590, 3,865,693 and 3,977,942, British Pat. No. 1,425,081, Japanese Patent Publication Nos. 69294/75 and 110097/76 and Japanese Patent Application (OPI) No. 49071/77.

It is strongly desired to produce Cephamycin C using microorganisms in much better yield with easier operation.

After extensive research it has been found that a new strain Streptomyces sp. OFR 1022 isolated from the soil in Kenya produces a great amount of Cephamycin C in a culture medium and enables to advantageously produce Cephamycin C on a commercial scale. On the basis of the new findings, this invention has been completed.

SUMMARY OF THE INVENTION

This invention provides a process for the production of Cephamycin C which comprises cultivating a strain of Streptomyces sp. OFR 1022 in a culture medium to accumulate therein Cephamycin C and recovering said Cephamycin C.

DETAILED DESCRIPTION OF THE INVENTION

Figure 1A:
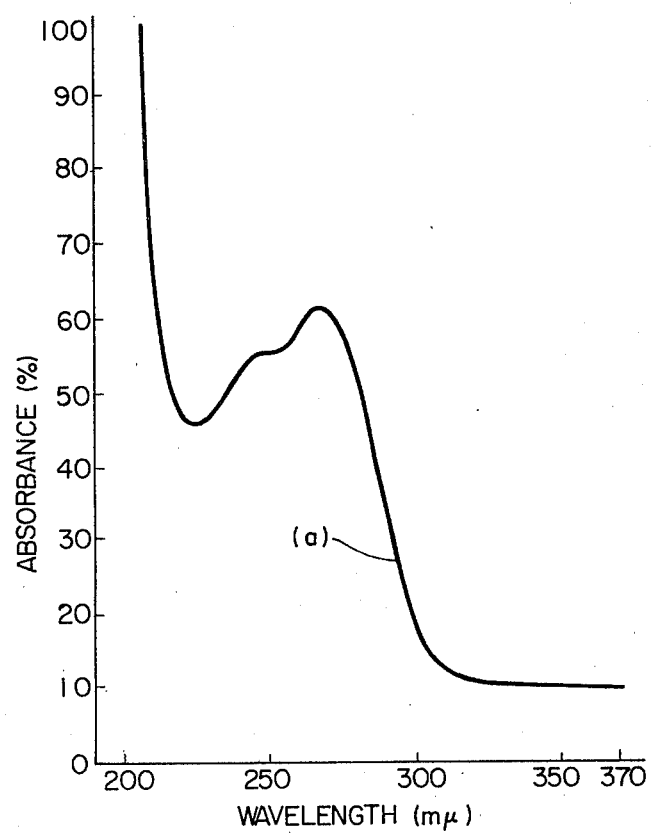
FIGS. 1A and 1B are ultraviolet absorption spectra of Cephamycin C obtained by the process of this invention.

The new strain Streptomyces sp. OFR 1022 for use in this invention has an outstandingly excellent Cephamycin C productivity in comparison with known Cephamycin C producing strains and furthermore the optimal cultural temperature therefor is high in comparison with those for the known strains. In accordance with the process of this invention, therefore, it is possible to produce Cephamycin C, without applying any cooling operation and by use of simplified operation and apparatuses, with ease, in a markedly great amount, at a low cost and in good yield.

Thus this invention provides a markedly effective process for the production of Cephamycin C.

The microbiological properties of the strain Streptomyces sp. OFR 1022 for use in this invention are as follows:

(I) Morphological Features

The observation results of the strain after the cultivation thereof at 28° C. for 3 weeks are as follows:

The aerial mycelium consists of the main axis and simple branches along the main axis. These branches often form clusters. On the culture medium which permits spore formation, the branch is rarely in a loop form and usually in a completely spiral form wherein it is closed wound several times. The spore has a spiny surface, and it is spherical or elliptical in shape and $0.7–1.0\mu \times 1.1–1.3\mu$ in size. Ten or more spores are formed in a chain form.

(II) Cultural Characteristics on Various Agar Media

The observation results of the strain after the cultivation thereof at 28° C. for 3 weeks are shown in Table 1. The tone is determined by reference to *Color Harmony Manual*, Container Corporation of America, Chicago.

TABLE 1

| Culture Medium | Growth | Aerial Mycelium | Substrate Mycelium | Reverse Side | Soluble Dye |
|---|---|---|---|---|---|
| Sucrose Nitrate Agar | Moderate | Moderate Powdery Natural, 2dc | Light Ivory, 2ca | Bamboo, 2gc | None |
| Glucose Asparagine Agar | Moderate | Abundant Velvet-like Covert Tan, 2ge-Beige, 3ge | Pearl Pink, 3ca | Pearl Pink, 3ca | None |
| Glycerin Asparagine Agar | Good Somewhat Sparse (Peripheral) | Abundant Velvet-like Silver Gray 3fe -Beige Brown 3ig | Mustard Tan, 2lg | Adobe Brown, 3lg | Trace of Yellow |
| Starch Inorganic Salts Agar | Good | Abundant Velvet-like Silver Gray, 3fe | Mustard Tan, 2lg | Adobe Brown, 3lg | None |
| Culture Medium | Growth | Aerial Mycelium | Substrate Mycelium | Reverse Side | Soluble Pigment |
| Tyrosine Agar | Moderate | Abundant Velvet-like | Adobe Brown, 3lg | Clove Brown, 3ni | Adobe Brown, |

TABLE 1-continued

| | | | | | |
|---|---|---|---|---|---|
| Nutrient Agar | Poor | Natural, 2dc None | Bamboo, 2gc | Ivory Tint, 2cb | 31g None |
| Yeast Malt Agar | Good | Abundant Velvet-like White | Camel, 3ie | Cinnamon, 31e | None |
| Oatmeal Agar | Good Sparse (Peripheral) | Abundant Powdery Beige Brown, 3ig | Ivory Tint, 2cb | Silver Gray, 3fe | None |
| Peptone Yeast Iron Agar | Moderate-Poor | None | Beige Brown, 3ig | Covert Tan, 2ge | Deep Brown, 3pl |

(III) Physiological Properties

| | | |
|---|---|---|
| (1) | Growth Temperature Range | 15° C. to 46° C. (optimal growth temperature about 37° C.) |
| (2) | Growth pH Range | pH 4.5 to pH 8.5 (optimal growth pH about 6.5) |
| (3) | Liquefaction of Gelatin (in a glucose-peptone-gelatin medium, 20° C.) | Negative |
| (4) | Hydrolysis of Starch (in a starch-inorganic salts agar medium) | Positive |
| (5) | Coagulation and Peptonization of Skim Milk | Peptonization |
| (6) | Production of Melanoid Pigment | Positive (in a tyrosine-agar, a peptone-yeast-iron-agar, and a tryptone yeast extract broth) |
| (7) | Reduction of Nitrates | Negative |
| (8) | Decomposition of Celluloses | Negative |
| (9) | NaCl Tolerance | Grow at 3% and not grow at 5%. |

(IV) Utilization of Carbon Sources (on a Pridham-Gottlieb agar medium)

| | |
|---|---|
| L-Arabinose | ± |
| D-Xylose | + |
| D-Glucose | ++ |
| D-Fructose | + |
| Sucrose | ++ |
| Inositol | ++ |
| L-Rhamnose | − |
| Raffinose | ± |
| D-Mannitol | ++ |

(Note: ++: Well utilized; +: utilized; ±: slightly utilized; −: not utilized)

(V) Diaminopimelic Acid in Cell Wall

LL-Diaminopimelic Acid

The present OFR 1022 belongs to the genus Streptomyces; according to the International Streptomyces Project (ISP) method, the morphology of spore-forming mycelium belongs to that of the section Spirales, the surface of the spore is spiny, the color of the matured aerial mycelium is of the Gray color series, and it produces a melanoid pigment, but almost no other pigments. Furthermore, taking into consideration the fact that the substrate mycelium and the reverse side are pale yellow—yellow brown or light brown in color, and the various data as described above, such as the physiological properties and utilization of carbon sources, the present strain has been assigned to a strain most similar to *Streptomyces filipinensis* and *Streptomyces gannmycicus* according to *Bergey's Manual of Determinative Bacteriology* 8th Ed. (1974), S. A. Waksman, *The Actinomycetes*, Vol. 2, (1961), and E. B. Shirling and D. Gottlieb, *International Journal of Systematic Bacteriology*, Vol. 18, pp. 69 to 189 (1968), Vol. 18, pp. 279 to 392 (1968), Vol. 19, pp. 391 to 512 (1969) and Vol. 22, pp. 265 to 394 (1972).

Therefore, the present strain and the type strains similar to the present strain were cultivated under the same conditions and compared. The results are shown in Table 2.

TABLE 2

| | Streptomyces sp. OFR 1022 | Streptomyces filipinensis ISP 5112 | Streptomyces gannmycicus ISP 5572 |
|---|---|---|---|
| Form of Aerial Mycelium | Simple branches are formed along the main axis, aerial mycelium, often form cluster, are closed spiral wound several times in the top end thereof, and rarely in a loop form. | Tuft, tight spiral, loop or hook-like in the top end. | Simple branch. The top end is mainly RF, rarely in an open spiral or tight spiral. |
| Sucrose Nitrate Agar Growth | Moderate, light ivory, 2ca | Good, pastel yellow, 1db | Poor, colorless |
| Aerial Mycelium | Moderate, powdery, natural, 2dc | Moderate, powdery white | None |
| Reverse Side | Bamboo, 2gc | Bamboo, 2gc | Colorless |
| Soluble Pigment | None | None | None |

TABLE 2-continued

|  | Streptomyces sp. OFR 1022 | Streptomyces filipinensis ISP 5112 | Streptomyces gannmycicus ISP 5572 |
| --- | --- | --- | --- |
| Glucose Asparagine Agar |  |  |  |
| Growth | Moderate pearl pink, 3ca | Good mustard brown, 2pl | Good mustard, 2le |
| Aerial Mycelium | Abundant velvet-like covert tan, 2ge to beige, 3ge | Abundant powdery natural, 2dc to covert gray, 2fe | Moderate powdery covert gray, 2fe |
| Reverse Side | Pearl pink, 3ca | Beige brown, 3ig | Yellow maple, 3ng |
| Soluble Pigment | None | Trace of yellow | Trace of yellow |
| Nutrient Agar |  |  |  |
| Growth | Poor bamboo, 2gc | Moderate, poor straw, 2fb | Moderate bamboo, 2gc |
| Aerial Mycelium | None | None | Poor, white |
| Reverse Side | Ivory tint, 2cb | Ivory, 2db | Cream, 1½ ca |
| Soluble Pigment | None | None | None |
| Peptone Yeast Iron Agar |  |  |  |
| Growth | Moderate to poor beige brown, 3ig | Moderate light mustard tan, 2ie | Good bamboo, 2gc |
| Aerial Mycelium | None | None | Poor, white |
| Reverse Side | Covert tan, 2ge | Covert tan, 2ge | Light apricot, 2ea |
| Soluble Pigment | Deep brown, 3pl | Yellow maple, 3ng | Trace of brown |
| Physiological Properties |  |  |  |
| Upper Limit of Growth Temperature | Grow at 46° C. and not grow at 60° C. | Grow at 46° C. and not grow at 60° C. | Grow at 42° C. and not grow at 46° C. |
| Growth pH Range | 4.5–8.5 | 4.5–10.5 | 4.5–11.0 |
| Liquefaction of Gelatin | Negative | Negative | Positive |
| Hydrolysis of Starch | Positive | Positive | Positive (strong) |
| Peptonization of Skim Milk | Positive | Positive | Positive (strong) |
| Melanoid Pigment Production Capability |  |  |  |
| Tryptone Yeast Extract Broth | + | + | ± |
| Peptone Yeast Iron Agar | +++ | + | + |
| Tyrosine Agar | ++ | + | + |
| Reduction of Nitrates | Negative | Positive | Positive (weak) |
| Utilization of Carbon Sources |  |  |  |
| L-Arabinose | ± | ++ | ++ |
| D-Xylose | + | + | + |
| D-Glucose | ++ | ++ | ++ |
| D-Fructose | + | ++ | ++ |
| Sucrose | ++ | ++ | − |
| Inositol | ++ | ++ | ++ |
| L-Rhamnose | − | − | ++ |
| Raffinose | ± | ++ | ++ |
| D-Mannitol | ++ | ++ | ++ |

NOTE:
++: well utilized;
+: utilized;
±: slightly utilized;
−: not utilized

Table 2 indicates:

(1) The present strain OFR 1022 is different from Streptomyces filipinensis ISP 5112 in that in the Streptomyces filipinensis ISP 5112, the aerial mycelium is in a tuft form and the top end thereof is tight spiral and in a loop form or hook-like form, the color of the substrate mycelium on the glucose-asparagine-agar medium is mustard brown 2pl, the reverse side is beige brown 3ig, and it has the nitrate reduction capability and well utilizes L-arabinose and raffinose; and (2) The present strain OFR 1022 is different from Streptomyces gannmycicus ISP 5572 in that the major portion of the aerial mycelium of the Streptomyces gannmycicus ISP 5572 is in the form of the section RF (Rectiflexibiles) and it is rarely in the somewhat opened spiral or tight spiral form, the growth on the sucrose-nitrate-agar medium is poor and no development of aerial mycelium is observed, on the other hand the development of aerial mycelium on nutrient agar medium and peptone-yeast-iron agar medium is observed, and furthermore it cannot grow at 46° C., can liquefy gelatin and has the carbon source utilization capability, particularly well utilizes L-arabinose, L-rhamnose and raffinose, but does not utilize sucrose.

Thus it can be seen that the present strain OFR 1022 is a novel strain which is different from Streptomyces filipinensis and Streptomyces gannmycicus, to which the present strain is most similar.

The present strain OFR 1022 has been designated as Streptomyces sp. OFR 1022 and deposited in the Fermentation Research Institute, the Agency of Industrial Science and Technology, Ibaragi, Japan under the microorganism deposit number of FERM-P No. 4985 and in American Type Culture Collection, 12301 Parklawn Drive, Rockville, Md. 20852, U.S.A. under deposit number of ATCC 31666, received by the American Type Culture Collection on June 24, 1980.

It is essential to the present invention to utilize the Streptomyces sp. OFR 1022 or the natural or artificial mutants thereof. The cultivation of the present strain or the mutants thereof can be carried out by a conventional cultivation method, preferably in a liquid culture medium by the shaking cultivation or the aerated stirring cultivation.

Various known nutrients for actinomycetes can be used for the cultivation of the present strain. Nutrients which can be used as carbon sources include glucose, sucrose, glycerin, maltose, dextrin, starch, soybean oil, cotton seed oil and the like. Nutrients which can be used as nitrogen sources include soybean flour, peanut flour, cotton seed flour, yeast, fish flour, corn steep liquor, peptone, yeast extract, meat extract, oatmeal, casein hydrolyzate, sodium nitrate, ammonium nitrate, ammonium sulfate and the like. Inorganic salts include magnesium sulfate, salt, phosphoric acid salts, calsium carbonate and the like.

To the culture medium can be, if necessary or desired, added a small amount of a metal salt and suitable amounts of amino acids such as α-aminoadipic acid, sodium thiosulfate, sodium dithionite, glycine, L-phenylalanine, arginine and ornithine and diamines such as 1,3-diaminopropane, 1,3-diamino-2-hydroxypropane, polyamines such as spermidine and the like. In the case of the liquid cultivation, silicone, vegetable oil, surfactants and the like can be added as defoaming agents.

The pH of the culture medium is from about 4.0 to about 8.0, preferably about 6.0 and the cultivation temperature is from about 15° C. to about 46° C., preferably about 37° C. The maximum production amount of the desired Cephamycin C can be usually obtained in a period of from 72 hours to 96 hours. For Example, in the cultivation in a 5 liter volume minijar fermenter, the amount of Cephamycin C to be accumulated reaches about 2 mg/ml. The Cephamycin C is mainly present in a liquid portion of the culture solution because it is well soluble in water.

After the cultivation is completed, the mycelia and other solids are removed by centrifugal separation or filtration, and the Cephamycin C present in the filtrate is easily isolated and purified by a conventional operation utilizing the physical and chemical characteristics. For such purification, there can be effectively used a method wherein various adsorbents such as an ion exchange resin, silica gel and active carbon are used. Examples of such ion exchange resins are acidic cation exchange resins and basic anion exchange resins. Strongly basic anion exchange resins are preferably used. Representative examples are Diaion PA 406 (produced by Mitsubishi Chemical Co., Ltd.), Dowex 50W×4 (produced by Dow Chemical Corp.), Dowex 1×2 (produced by Dow Chemical Corp.), etc.

The Cephamycin C adsorbed on the adsorbent is eluted by use of water, brine, a methanol-water mixed solution, a n-butanol-water mixed solution, an acetone-water mixed solution or the like.

For the purifaction of the Cephamycin C, a chromatgraphic method using silica gel or Avicel (produced by Asahi Kasei Kogyo, K.K.) can be employed.

By appropriately combining the purification methods as described above and repeating such a combination, pure Cephamycin C can be obtained.

The physical and chemical properties of the Cephamycin C obtained by this invention are shown below:

(1) Appearance
   White Powder (2) Specific Rotation
   $[\alpha]_D^{20} = 221°$ (C=0.4, $H_2O$)

(3) Solubility
   Soluble in water, sparingly soluble in ethanol, and slightly soluble in dimethylsulfoxide.

(4) Color Reaction
   Positive to the ninhydrin reaction and the iodo reaction, and negative to the ferric chloride reaction.

(5) Thin Layer Chromatography (TLC)
   The development was carried out using a solution of n-butanol:acetic acid:water=2:1:1 (V/V) on a thin layer chromatographic plate, Silica Gel GF 254 (produced by Merk and Co.). Rf=0.2

Figure 1B:
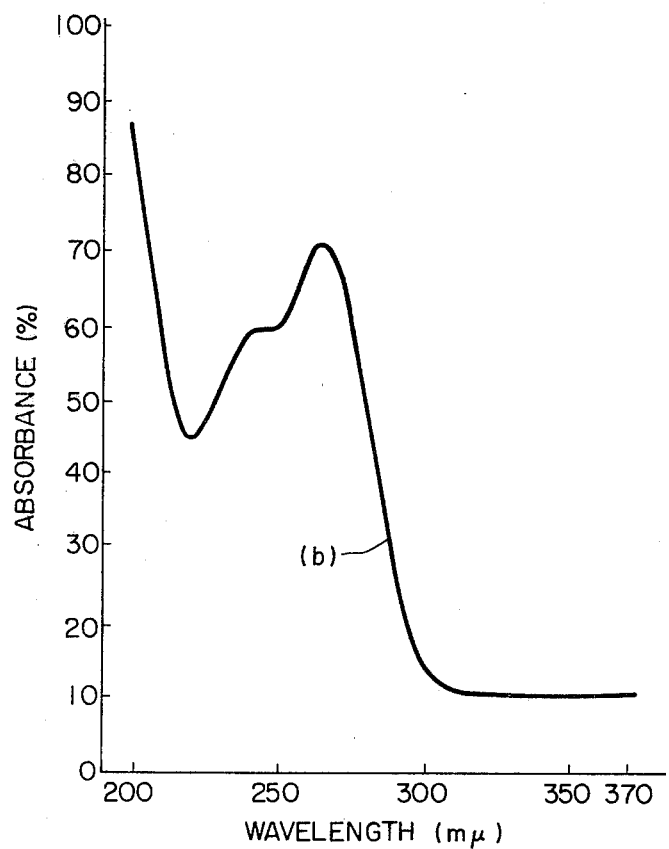

(6) Ultraviolet Absorption Spectrum (UV)
   As illustrated by Curve (a) (solvent $H_2O$) in FIG. 1A and Curve (b) (solvent 0.1 N HCl) in FIG. 1B. The maximum absorption and the $E_{1\ cm}^{1\%}$ value in each solvent are shown in Table 3.

TABLE 3

| Solvent | Maximum Absorption (mμ) | $E_{1\ cm}^{1\%}$ Value |
| --- | --- | --- |
| $H_2O$ | 240 | — |
|  | 265 | 127 |
| 0.1 N HCl | 245 | — |
|  | 266 | 105 |

Figure 2:
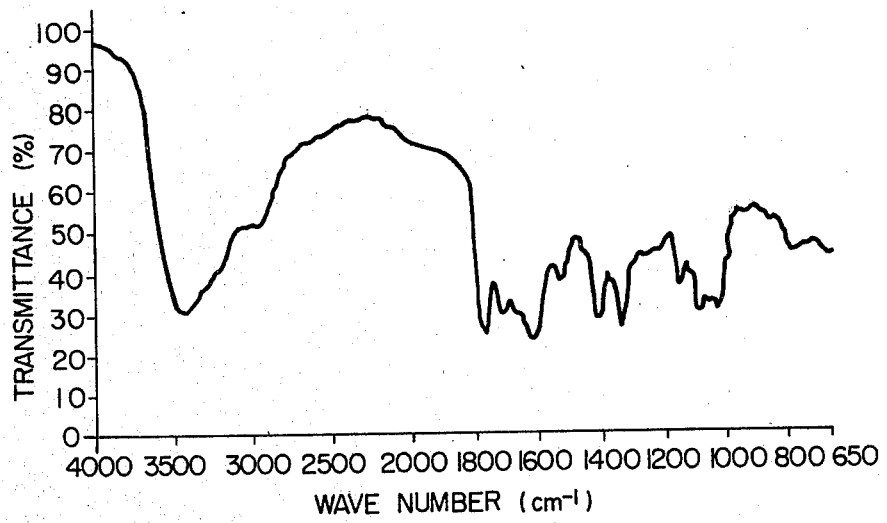
FIG. 2 is an infrared absorption spectrum of said Cephamycin C.

(7) Infrared Absorption Spectrum (IR)
   The IR spectrum (KBr tablet) is illustrated in FIG. 2.

Figure 3:
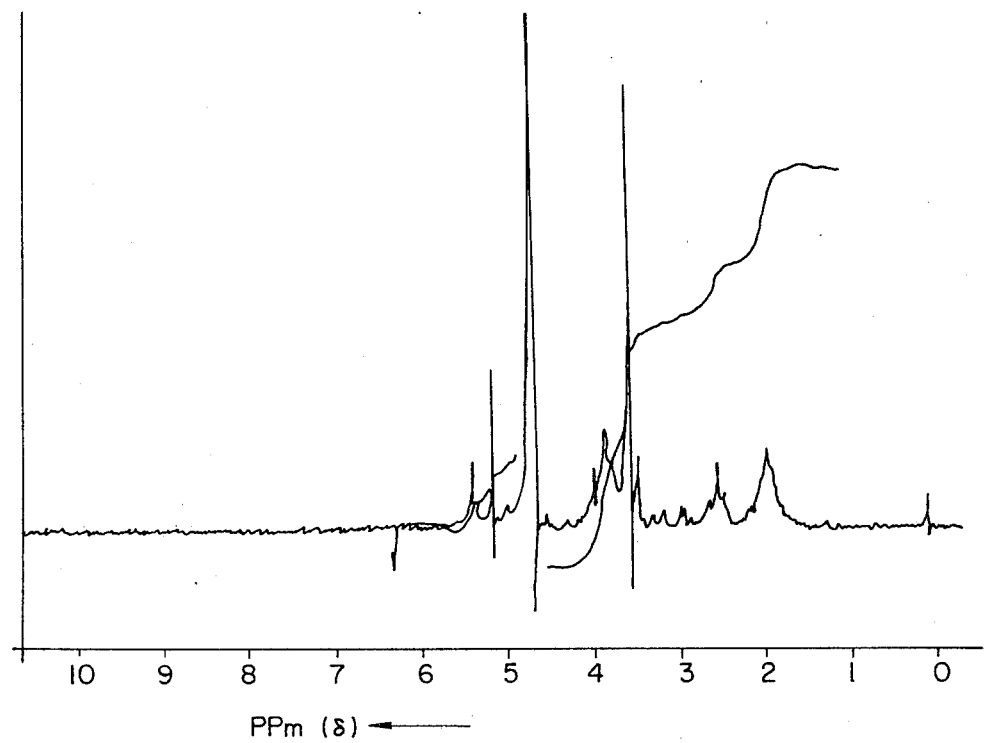
FIG. 3 is a proton nuclear magnetic resonance (NMR) spectrum of said Cephamycin C.

(8) Proton Nuclear Magnetic Resonance (NMR) Spectrum
   The NMR spectrum is shown in FIG. 3, in which $D_2O$ was used as a solvent and DSS was used as an inner standard reagent and the frequency was 60 MHz.

(9) Amino Acid Analysis
   The analysis after the hydrolysis with 4 N HCl at 110° C. for 4 hours confirmed that α-aminoadipic acid and glycine were formed.

The antimicrobial spectra to various microorganisms of the Cephamycin C produced by the process of this invention are shown as minimum inhibitory concentrations (MIC) in Table 4.

TABLE 4

| Test No. | Test Organisms | MIC (μg/ml) |
| --- | --- | --- |
| 1 | Bacillus subtilis PCI 219 | 15.6 |
| 2 | Staphylococcus aureus FDA 209P | 250 |
| 3 | Staphylococcus aureus Newman | 250 |
| 4 | Sarcina lutea PCI 1001 | 15.6 |
| 5 | Salmonella typhi 0-901 NCTC 8393 | 3.9 |
| 6 | Proteus vulgaris IID OX-19 | 7.8 |
| 7 | Proteus mirabilis 1287 | 7.8 |
| 8 | Esherichia coli NIHJ | 15.6 |

The above physical and chemical properties, and the antimicrobial spectra are in good agreement with those of the known Cephamycin C as described, for example, in Japanese Patent Application (OPI) No. 3286/1971.

The following examples are given to illustrate this invention in greater detail, but this invention is not limited thereto. All percents (%) are by weight.

EXAMPLE 1

Streptomyces sp. OFR 1022, which had been incubated on an oatmeal agar medium, was inoculated on a liquid culture medium containing 3% of starch, 0.5% of sucrose, 1% of soybean flour and 0.3% of dry yeast and having a pH of 7 and incubated with shaking at 37° C. for 48 hours to give a seed culture solution.

In a 30 liter volume jar fermenter was placed 20 l of culture medium containing 3% of starch, 1% of sucrose, 2% of cotton seed flour, 1% of dry yeast, 0.05% of magnesium sulfate, 0.02% of potassium dihydrogenphosphate, 0.05% of disodium monohydrogenphosphate and 0.5% of silicone (produced by Shinetsu Chemical Co., Ltd.) as a defoaming agent (after sterilization, pH=6.0), on which the above seed culture solution was then inoculated at a ratio of 1% and incubated with aeration at 37° C. The amount of the air aerated was 20 l/min and the number of rotation of a propeller was 300 r.p.m.

After the cultivation for 90 hours, the amount of the Cephamycin C produced reached 2 mg/ml. This was determined by use of high speed liquid chromatography under the following measuring conditions:
Pump: (Japan Waters Co., Ltd. 6000 A type)
Injector: (Japan Waters Co., Ltd. U6K type)
Detector: (Shimazu Seisakusho Ltd. SPD 1)
Column: (Japan Waters: Micro-Bandapack C-18, 4 mmid × 30 cm)
Mobile Phase: 0.01 M—acetic acid
Flow Rate: 2 ml/min.
Detection: UV 254 nm 0.16 AUFS
Chart Speed: 0.5 cm/min.

After the cultivation was completed, the culture solution was subjected to centrifugal separation to remove the mycelia and the filtrate in the amount of 18 l was adjusted to pH 7 to 8 and adsorbed on 3 l of Diaion PA 406. Then it was eluted (with 0.5 M of sodium chloride aqueous solution) to obtain 2 l of an antimicrobial active fraction. This fraction was concentrated under reduced pressure at about 30° C. The concentrated solution in the amount of 200 ml was passed through 400 ml of Silica Gel ODS (produced by Waters Co.) and then again concentrated. The thus concentrated solution was subjected to reverse phase chromatography with 0.01 M acetic acid on a 5.35 cm$\phi$ × 120 cm long column of Silica Gel ODS.

Active fractions were collected and freeze-dried to obtain 18 g of white powdery Cephamycin C. The physical and chemical properties of the obtained compound were examined and found to be the same as described above.

EXAMPLE 2

Streptomyces sp. OFR 1022 was cultivated in the same manner as in Example 1 and the culture broth was filtered to obtain 20 l of filtrate. The filtrate was adsorbed on 1.5 l of Diaion PA 406 C$_1$ type (produced by Mitsubishi Chemical Co., Ltd.). Then the column was washed deionized water in an amount of 4 times as large as the volume of the column and was eluted with 1 M aqueous NaCl solution to obtain 2.5 l of antimicrobial active fraction. This fraction was adjusted to pH of 1 with 4 N hydrochloric acid and NaCl was added so that the final concentration became 4 M (moles/l). The resulting solution was adsorbed on a column (2 l) of Diaion HP 20 (produced by Mitsubishi Chemical Co., Ltd.) and eluted with water. The objective compound Cephamycin C came to be eluted when the pH of the eluate reached about 4. Thereafter, eluate was collected until the amount thereof amounted to 1.5 l and freeze-dried to obtain 24 g of white powder of Cephamycin C.

The physical and chemical properties of the obtained compound were examined and found to well coincide with those described in Example 1.

The productivity of Cephamycin C of the present strain OFR 1022 was compared with those of the known strains reported in the various references as illustrated in Table 5 below.

TABLE 5

| Strain | Broth Yield of Cephamycin C | Reference |
| --- | --- | --- |
| Streptomyces jumonjiensis | 40 mg/l | U.S. Pat. No. 3,865,693 |
| Streptomyces lactamgenes | 200 mg/l | Japanese Patent Application (OPI) 69294/75 |
| Streptomyces sp. P6621 | 350 mg/l | Japanese Patent Application (OPI) 110097/76 |
| Streptomyces clavuligerus | 494 mg/l | U.S. Pat. No. 3,977,942 |
| Streptomyces lactamgenes | | |
| " | 1291 mg/l | U.S. Pat. No. 3,770,590 |
| " | 530 mg/l | Japanese Patent Application (OPI) 49071/77 |
| Streptomyces sp. OFR 1022 | 2000 mg/l | Present Invention |

From Table 5 above it can be seen that Streptomyces sp. OFR 1022 used in the present invention has excellent yield of Cephamycin C as compared with the prior art strains of Streptomyces.

While the invention has been described in detail and with reference to specific embodiments thereof, it will be apparent to one skilled in the art that various changes and modifications can be made therein without departing from the spirit and the scope thereof.

What is claimed is:

1. A process for producing Cephamycin C which comprises cultivating Streptomyces sp. OFR 1022 in a culture medium to accumulate therein Cephamycin C and recovering said Cephamycin C.

2. The process of claim 1 wherein said microorganism is cultivated at a temperrature of 15° C. to 46° C.

3. The process of claim 2 wherein said microorganism is cultivated at a temperature of 37° C.

* * * * *